US010736602B2

(12) United States Patent
Gubbini et al.

(10) Patent No.: US 10,736,602 B2
(45) Date of Patent: Aug. 11, 2020

(54) ULTRASOUND PROBE

(75) Inventors: Alessandro Gubbini, State College, PA (US); William R. Dreschel, State College, PA (US)

(73) Assignee: BK Medical Holding Company, Inc., Peabody, MA (US)

( * ) Notice: Subject to any disclaimer, the term of this patent is extended or adjusted under 35 U.S.C. 154(b) by 1964 days.

(21) Appl. No.: 13/256,447

(22) PCT Filed: Jun. 24, 2009

(86) PCT No.: PCT/US2009/048374
§ 371 (c)(1),
(2), (4) Date: Sep. 14, 2011

(87) PCT Pub. No.: WO2010/114573
PCT Pub. Date: Oct. 7, 2010

(65) Prior Publication Data
US 2012/0022379 A1    Jan. 26, 2012

Related U.S. Application Data

(60) Provisional application No. 61/165,630, filed on Apr. 1, 2009.

(51) Int. Cl.
*A61B 8/00* (2006.01)
*A61B 8/12* (2006.01)
*A61B 8/08* (2006.01)
(52) U.S. Cl.
CPC .................. *A61B 8/00* (2013.01); *A61B 8/12* (2013.01); *A61B 8/4254* (2013.01);
(Continued)

(58) Field of Classification Search
CPC ....... A61B 8/00; A61B 8/4477; A61B 8/4254; A61B 8/546; A61B 8/483; A61B 8/467;
(Continued)

(56) References Cited

U.S. PATENT DOCUMENTS 4,785,819 A * 11/1988 Pearce ................. G10K 11/355
600/446
4,917,097 A *  4/1990 Proudian et al. ............. 600/463
(Continued)

FOREIGN PATENT DOCUMENTS

CN         1802124 A      7/2006
JP        2006271765     12/2006
(Continued)

OTHER PUBLICATIONS

International search report for PCT/US09/048374, published as WO 2010/114573.

*Primary Examiner* — Jeffrey G Hoekstra
*Assistant Examiner* — Jason M Ip
(74) *Attorney, Agent, or Firm* — Anthony M. Del Zoppo, III; Daugherty & Del Zoppo Co., LPA (57) ABSTRACT

An ultrasound imaging probe (101) includes a communications interface (107), including one or more ports (200-205), corresponding to one or more different communication protocols, for communication with ultrasound consoles. The probe (101) also includes a controller (106) that configures the probe (101) for communication with an ultrasound console (102) over a port (200-205) based on a communication between the communications interface (107) and a communications interface (110) of the console (102).

20 Claims, 7 Drawing Sheets

(52) U.S. Cl.
CPC .......... *A61B 8/4461* (2013.01); *A61B 8/4472* (2013.01); *A61B 8/4477* (2013.01); *A61B 8/4488* (2013.01); *A61B 8/467* (2013.01); *A61B 8/483* (2013.01); *A61B 8/546* (2013.01); *A61B 8/4455* (2013.01)

(58) Field of Classification Search
CPC ....... A61B 8/4472; A61B 8/4461; A61B 8/12; A61B 8/4488; A61B 8/4455
USPC ......................................................... 600/461
See application file for complete search history.

(56) References Cited

U.S. PATENT DOCUMENTS

| | | | |
|---|---|---|---|
| 5,181,514 A | | 1/1993 | Solomon et al. |
| 5,402,793 A | | 4/1995 | Gruner et al. |
| 5,630,417 A | | 5/1997 | Petersen et al. |
| 5,771,896 A | | 6/1998 | Sliwa, Jr. et al. |
| 6,364,839 B1 * | 4/2002 | Little ................... A61B 8/00 600/459 |
| 6,379,307 B1 * | 4/2002 | Filly ................... A61B 8/0833 600/461 |
| 6,478,743 B1 | | 11/2002 | Jordfald et al. |
| 6,569,097 B1 | | 5/2003 | McMorrow et al. |
| 7,211,045 B2 * | 5/2007 | Dala-Krish et al. .......... 600/441 |
| 8,038,619 B2 * | 10/2011 | Steinbacher ............. A61B 8/13 318/678 |
| 9,402,601 B1 * | 8/2016 | Berger ................. A61B 8/4472 |
| 2002/0016545 A1 | 2/2002 | Quistgaard et al. |
| 2003/0055338 A1 | 3/2003 | Steininger et al. |
| 2004/0015079 A1 | 1/2004 | Berger et al. |
| 2004/0236223 A1 * | 11/2004 | Barnes ................. A61B 5/0048 600/459 |
| 2005/0031239 A1 * | 2/2005 | Aoki ....................... F16C 33/76 384/448 |
| 2005/0049656 A1 * | 3/2005 | Petersen ............. A61N 1/37258 607/60 |
| 2005/0203400 A1 * | 9/2005 | Zappala et al. ............... 600/439 |
| 2006/0058654 A1 * | 3/2006 | Di Marco ................. A61B 8/00 600/437 |
| 2006/0065743 A1 * | 3/2006 | Fruhauf ................. G06F 13/385 235/492 |
| 2006/0100610 A1 * | 5/2006 | Wallace et al. .................... 606/1 |
| 2007/0038112 A1 * | 2/2007 | Taylor ..................... A61B 8/08 600/459 |
| 2007/0038113 A1 * | 2/2007 | Oonuki ................. A61B 8/0833 600/464 |
| 2007/0112266 A1 * | 5/2007 | Kishimoto ........... A61B 5/6843 600/437 |
| 2007/0239019 A1 | 10/2007 | Richard et al. |
| 2008/0126628 A1 * | 5/2008 | Mullis ................... G06F 9/4411 710/63 |
| 2008/0269664 A1 * | 10/2008 | Trovato et al. ................. 604/20 |
| 2009/0005687 A1 * | 1/2009 | Kawae ................. A61B 8/0833 600/461 |
| 2009/0036780 A1 | 2/2009 | Abraham |
| 2009/0036902 A1 | 2/2009 | DiMaio et al. ............... 606/130 |
| 2009/0099449 A1 * | 4/2009 | Lundberg ............... A61B 8/465 600/443 |
| 2010/0249589 A1 * | 9/2010 | Lysyansky et al. ......... 600/440 |

FOREIGN PATENT DOCUMENTS

| | | | |
|---|---|---|---|
| WO | 2008009044 A1 | | 1/2008 |
| WO | WO 2008009044 A1 * | | 1/2008 |
| WO | 2008146203 A1 | | 12/2008 |

* cited by examiner

ULTRASOUND PROBE

RELATED APPLICATION

This application is a national filing of PCT application Serial No. PCT/US09/048374, filed Jun. 24, 2009, published as WO2010/114573 on Oct. 7, 2010, which claims the benefit of priority of provisional patent application Ser. No. 61/165,630, filed on Apr. 1, 2009, confirmation number 4363, and entitled "ULTRASOUND PROBE," which is incorporated herein in its entirety by reference.

TECHNICAL FIELD

The following generally relates to ultrasound probes and more particularly to ultrasound probes configured for multi-dimensional imaging.

BACKGROUND

An ultrasound imaging probe generally includes one or more transducer arrays, affixed to a distal end of a mechanical device or a handle, and can be used for imaging of anatomical structures or organs. Volumetric imaging can be performed by using two-dimensional transducer arrays with no moving parts or by electromechanically moving a one-dimensional transducer array within the probe. Volumetric imaging has been used to visualize three-dimensional structures within the human body such as the kidneys, the uterus, a fetus, etc.

For patient imaging, the probe (and hence the transducer elements) is moved on the surface of the body over the structure of interest. The transducer generates a signal that traverses skin, subcutaneous fat, and/or bone material, reflects off the structure of interest, and is received back and detected at the transducer. The detected information is used to generate an image of the structure of interest. With other ultrasound applications (e.g., transabdominal, endovaginal, and endorectal), the transducer is positioned in and moved within a body cavity to image anatomical structures.

Unfortunately, some ultrasound probes are controllable only through ultrasound imaging systems and configured such that they only work with specific ultrasound imaging systems. As a consequence, a probe configured for multi-dimensional imaging may not be able to be used for multi-dimensional imaging when employed with an ultrasound imaging system that does not support multi-dimensional imaging applications. In addition, a probe configured with a particular interface may not be able to be used with a console that does not have a complementary interface. In addition, a console may lack suitable circuitry for controlling various components of a probe in communication therewith.

SUMMARY OF THE INVENTION

Aspects of the application address the above matters, and others.

In one aspect, an ultrasound imaging probe includes a communications interface with one port or a plurality of ports corresponding to one or more different communication protocols for communication with ultrasound consoles. The probe also includes a controller that configures the probe for communication with an ultrasound console over a port based on a communication between the communications interface and a communications interface of the console.

In a further aspect, an ultrasound probe includes a transducer array, an electromechanical drive system, a motor, and a controller that controls the drive system and motor to drive the transducer array to at least one of translate or wobble.

In a further aspect, a method includes identifying a type of communications interface of an ultrasound console in communication with an ultrasound imaging probe and selecting a communications port of the probe for communication between the probe and the console based on the identified type of communications interface.

In a further aspect, an ultrasound probe for three and/or four dimensional ultrasound applications includes a controller that configures the probe for use with a console that does not support three and/or four-dimensional ultrasound applications.

Those skilled in the art will recognize still other aspects of the present application upon reading and understanding the attached description.

DETAILED DESCRIPTION

Figure 1:
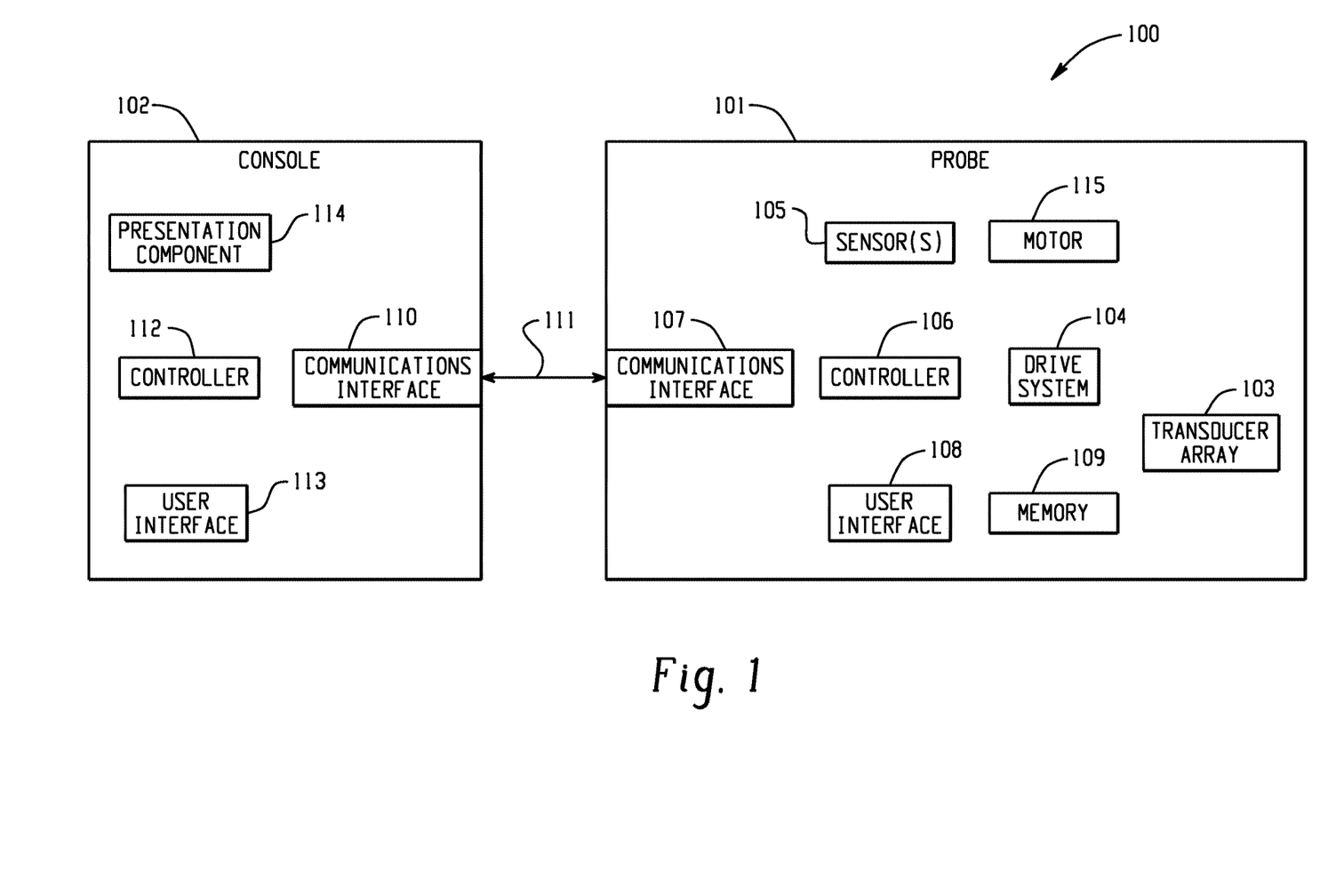
FIG. 1 illustrates an example probe and console of an imaging system.

FIG. 1 depicts an ultrasound imaging system 100 including a probe 101 and a console 102. The probe 101 is capable of multi-dimensional applications such as two, three and four-dimensional applications and includes a movable transducer array 103 having one or more transducer elements that transmit and detect signals. Non-limiting examples of suitable transducer elements include piezoceramic, MEMS and/or other transducer elements.

An electromechanical drive system 104 moves and/or orients the movable transducer array 103 through a motor 115. In one instance, this includes converting rotational motion of the motor 115 into translational, rotational and/or wobbling movement of the ultrasound transducer array 103. Suitable motors 115 may include but are not limited to a stepper motor, a DC motor, an ultrasonic motor, a piezo-electric motor, an electromagnetic motor, and/or other motor. The illustrated drive system 104 and motor 115 are configured to drive the transducer array 103 alternatively based on one or more predetermined and/or programmable movement patterns.

One or more sensors 105 sense information about the operating conditions of the probe 101. Suitable sensors include an optical or magnetic encoder that senses probe orientation; a temperature sensor that detects a temperature of the drive system 104, the transducer array 103 or one or more other components of the probe 101; a needle guide sensor that senses a needle guide coupled to the probe 101, and/or other sensor.

An integrated control circuit (also referred to herein as a µcontroller and a controller) 106 controls the drive system 104 and hence position of the transducer array 103. In one instance, the controller 106 controls the drive system 104 based on a mode of operation including a master, a slave, a self-booting, software loading, and/or other mode of operation and an application mode such as a two, three or four dimensional application. As described in greater detail below, the controller 106 identifies a suitable mode of operation and application mode based on a communication with the console 102. The controller 106 may also use the information sensed by the sensors 105 and/or user input to identify the mode and application.

A communications interface 107 is configured to receive and transmit information between the probe 101 and the console 102 and/or other device. As described in greater detail below, the interface 107 may be configured with a single communications port or with a plurality of communication ports for communicating with one or more different consoles 102 supporting different communication protocols. The interface 107 includes an analog portion for communication with analog components of the probe 101 and/or a digital portion for communication with digital components of the probe 101. For example, where the transducer array 103 is an analog transducer array, the analog portion is used to communicate with the transducer array 103, and where the drive system 104 is a digital drive system, the digital portion is used to communicate with the drive system 104.

A user interface 108 accepts user input and presents operational and/or application information in a human readable format. Examples of input include signals representing a particular mode of operation and/or application mode. In one embodiment, the user interface 108 accepts user input through a touch pad and/or predetermined control buttons. Additionally or alternatively, the user interface 108 includes an audio input for accepting voice commands or other audio information.

Memory 109 provides storage for data and/or other information, for example, configuration and/or imaging data from the transducer array 103 and/or data from the ultrasound console 102. The memory 109 may include software and/or firmware uploaded by a user. Such software and/or firmware may make the probe 101 specific to the user and/or supporting equipment.

It is to be appreciated that by incorporating the controller 106 in the probe 101 and allowing the configuration of different communication providing one or a plurality of different communication ports by the interface 107 allows the probe 101 to be used with essentially any console 102. For example, where the controller 106 is omitted from the probe 101, the probe 101 may only be employed with a console 102 having control circuitry compatible with or able to drive the drive system 104 and the motor 115 of the probe 101. In another example, where the communication interface 107 only supports a single type of port, the probe 101 may only be employed with a console 102 supporting that type of port.

The console 102 includes a communication interface 110. The probe 101 interfaces with the console 102 through the communication interface 110 over a channel 111, which may be a wired or wireless channel. The console 102 also includes a controller 112, which can send signals indicative of a selected mode of operation and/or application mode to the probe 101. A user interface 113 allows a user to communicate with the probe 101 through the console 102. A presentation component 114 presents image data.

Figure 2:
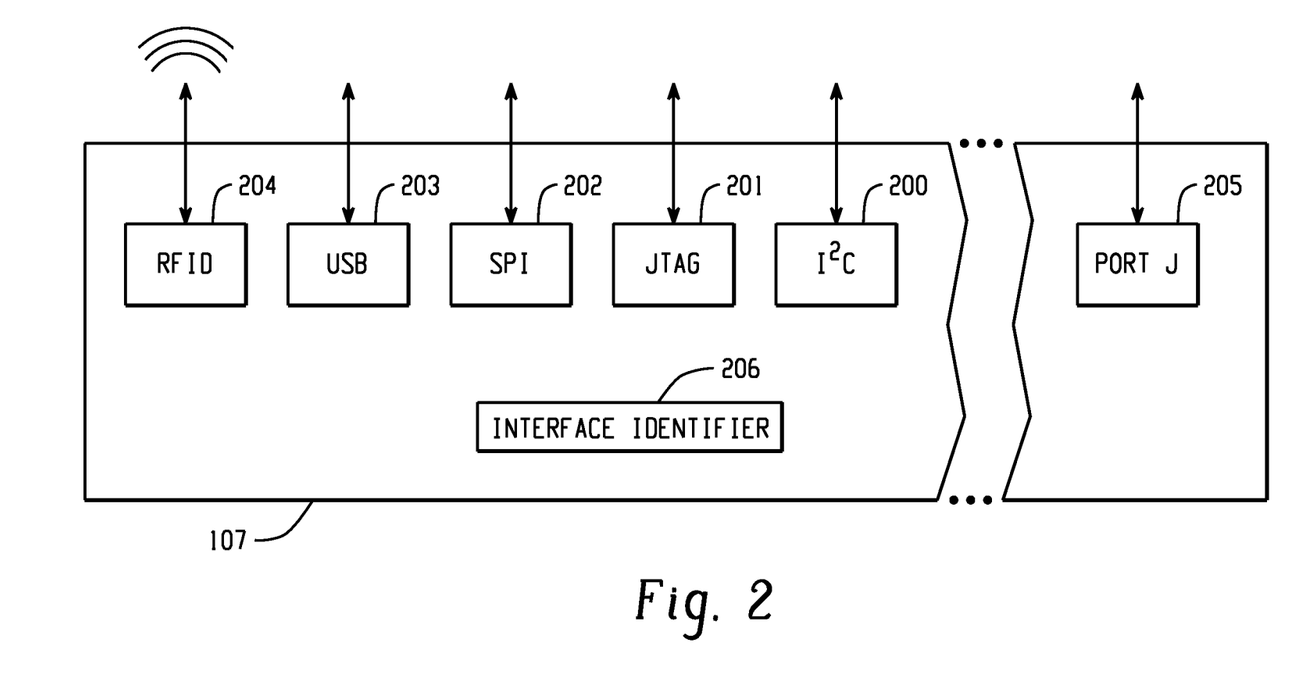
FIG. 2 illustrates an example communications interface of a probe.

With reference to FIGS. 1 and 2, FIG. 2 illustrates an example of the communications interface 107 with a plurality of communication ports.

In the illustrated example, the communications interface 107 includes an Inter-Integrated Circuit (I²C) port 200, which generally is a multi-master serial bus used to attach low-speed peripherals to an embedded system. The communications interface 107 further includes a Joint Action Test Group (JTAG) port 201, which is generally a test access port for debugging and probing printed circuit boards.

The communications interface 107 also includes a Serial Peripheral Interface (SPI) port 204, which generally is a synchronous serial data link that allows a single master device. The communications interface 107 further includes a Universal Serial Bus (USB) port 203, which is a standardized interface socket that generally allows connection of peripheral devices.

The communications interface 107 further includes a wireless port such as a Radio Frequency Identification (RFID) port 203. The communications interface 107 may also include one or more other ports (PORT J) 205.

An interface identifier 206 identifies the port in communication with the console 102 and generates a signal indicative thereof. The signal is provided to the controller 106, which configures the probe 101 for communication over the identified port.

Figure 3:
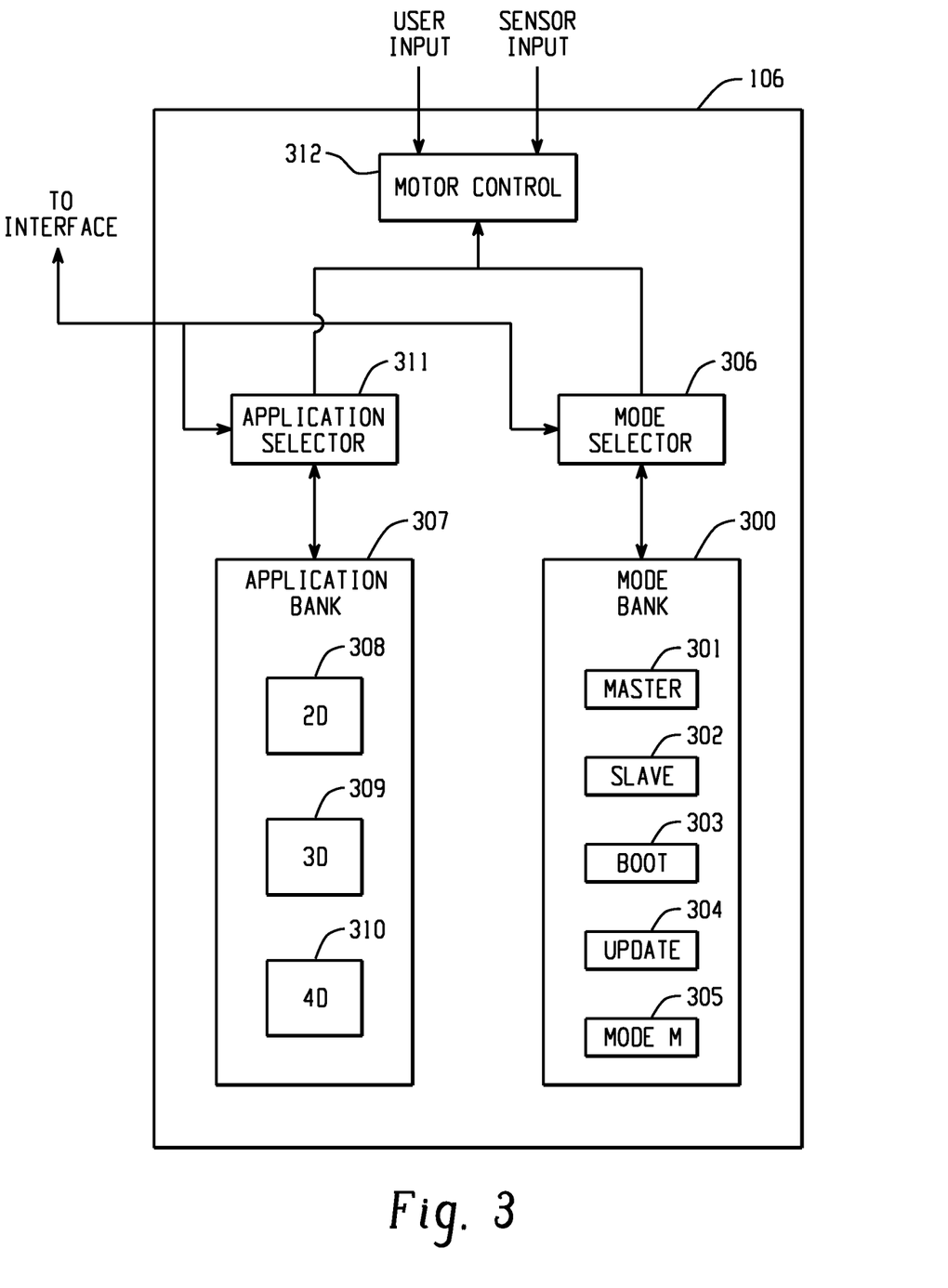
FIG. 3 illustrates an example probe controller logic.

With reference to FIGS. 1 and 3, FIG. 3 illustrates an example of the controller 106.

The controller 106 includes a mode bank 300 with one or more predetermined modes such as a master mode 301, a slave mode 302, a boot mode 303, an update mode 304, and one or more other modes 305. A mode selector 306 selects a mode of operation from the mode bank 300 based on various information.

The controller 106 also includes an application bank 307 with one or more predetermined application modes such as a two-dimensional mode 308, a three-dimensional mode 309, and a four-dimensional mode 310. An application selector 311 selects an application mode from the application bank 307 based on various information.

As described herein, the controller 106 configures the probe 101 based on a selected mode of operation, a selected application mode, information sensed by the sensor(s) 105, and a user input. In one instance, the controller 106 recognizes that the console does not support three or four-dimensional applications and configures the probe 101 so that the probe 101 can be used for three or four-dimensional applications using the user interface 108 of the probe 101. In this instance, the multi-dimensional imaging data may be stored in a memory 109 for subsequent retrieval.

A motion controller 312 generates a control signal for the drive system 104 based on the one or more of the selected operation mode, application mode, user input and/or sensor input. The control signal is indicative of movement and/or orientation of the transducer array 103.

Figure 4:
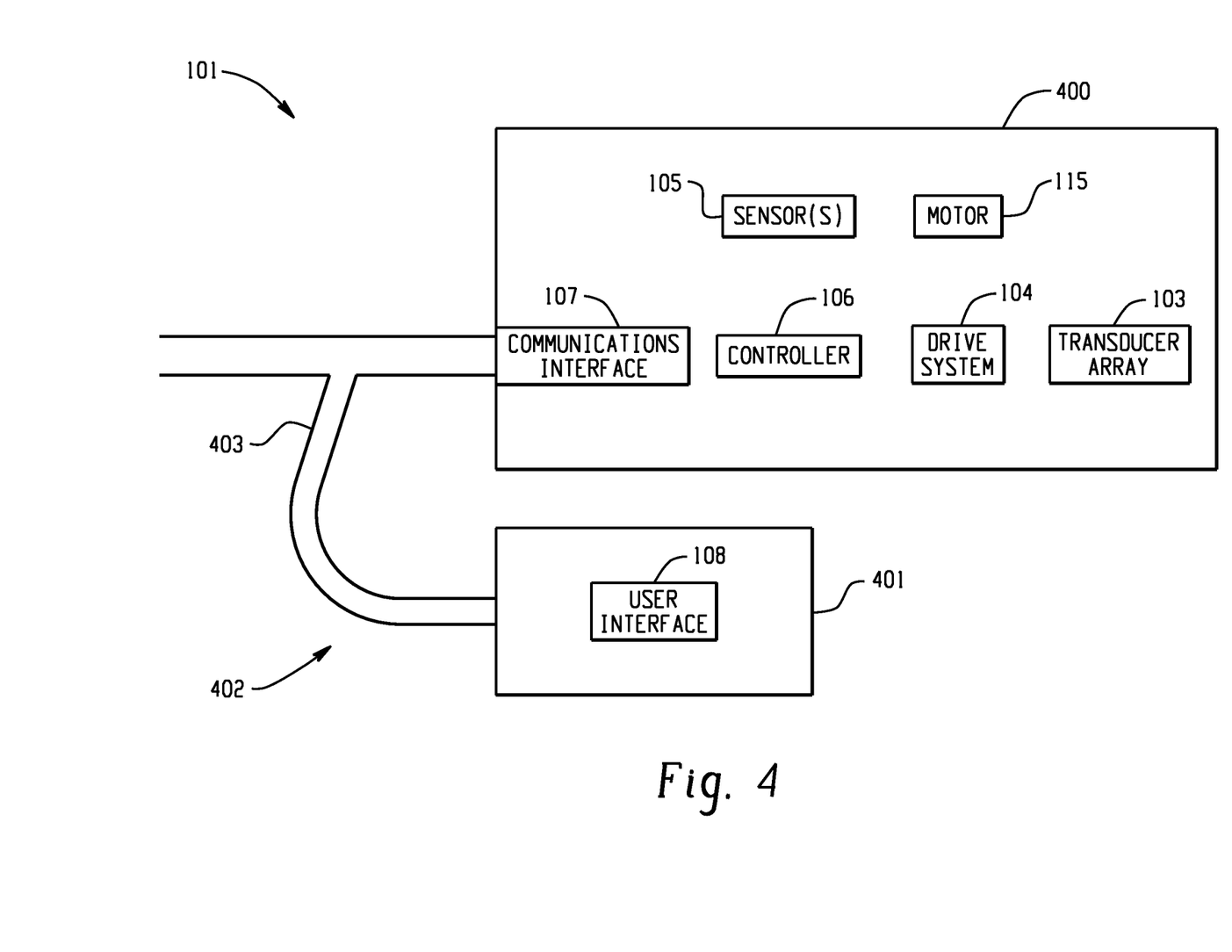
FIG. 4 illustrates an example probe with user controls in a dongle.
Figure 5:
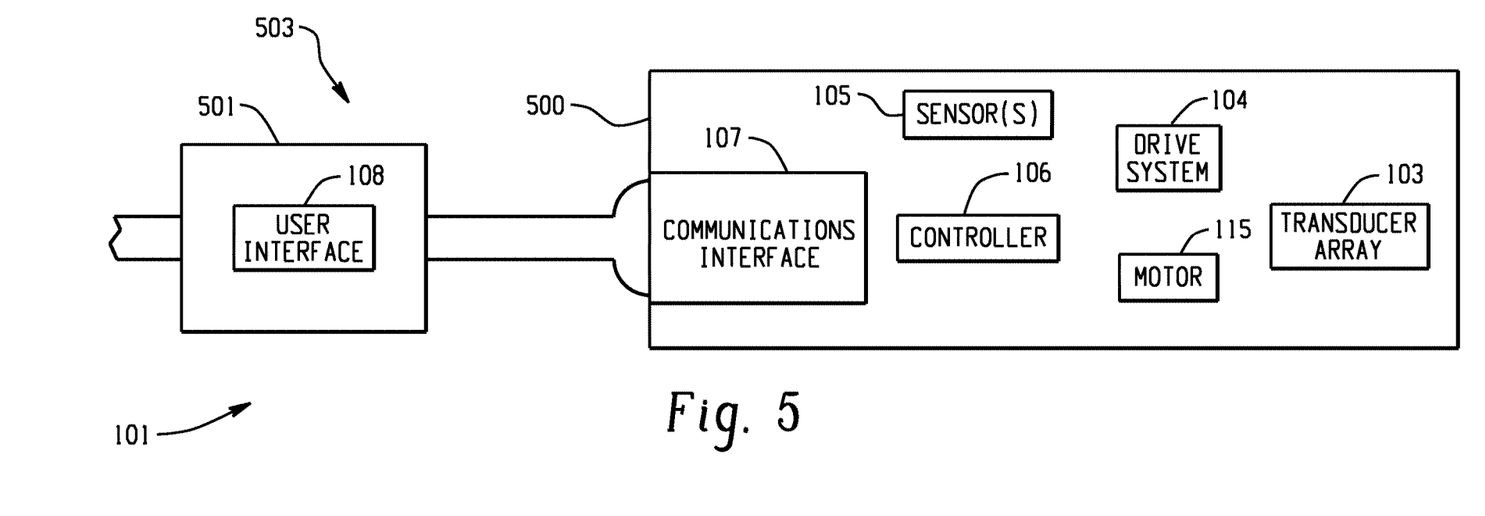
FIG. 5 illustrates an example probe with user controls in a cable.
Figure 6:
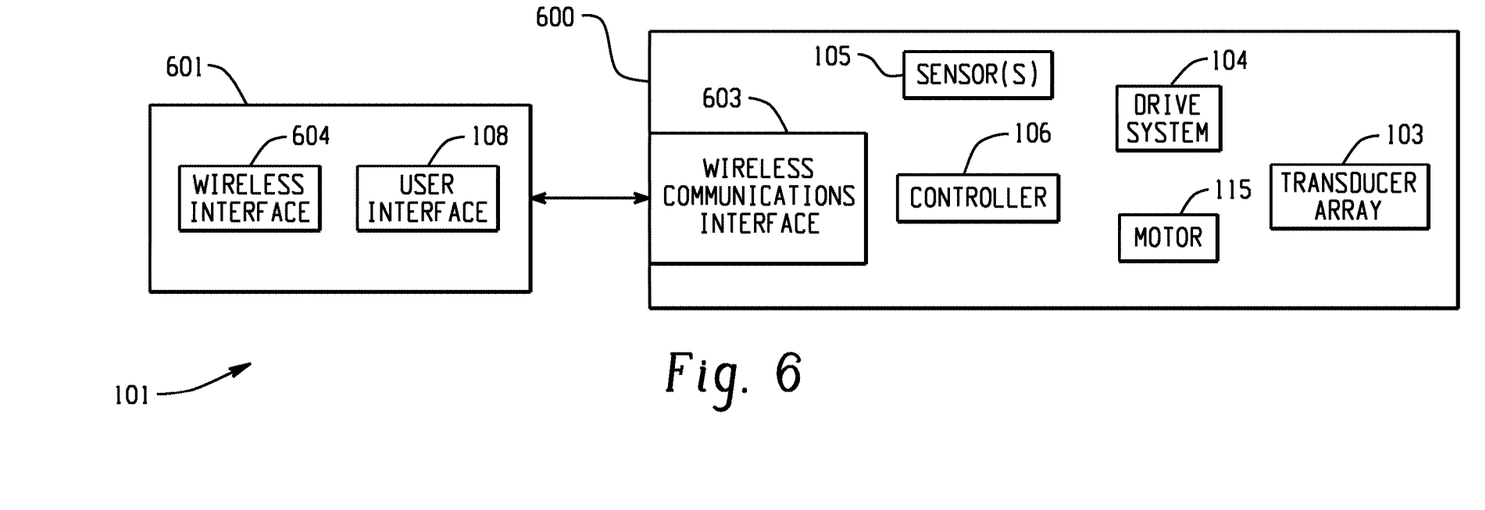
FIG. 6 illustrates an example probe with wireless control.

FIGS. 4, 5, and 6 depict alternative embodiments of the probe 101.

Initially referring to FIG. 4, the probe 101 includes first and second portions 400 and 401. The first portion 400 includes the transducer array 103, the drive system 104, the motor 115, the sensors 105, the controller 106, and the interface 107. The second portion 401 includes the user interface 108. The second portion 401 is part of dongle 402 and is connected to the first portion 400 through a connection 403, which can be a wired and/or wireless connection.

Turning to FIG. 5, the probe 101 includes first and second portions 500 and 501. The first portion 500 includes the transducer array 103, the drive system 104, the motor 115, the sensors 105, the controller 106 and the interface 107, and the second portion 501 includes the user interface 103. In this embodiment, the second portion 501 is integrated in or part of a cable 503, which is used to connect the probe 101 to the console 102.

In FIG. 6, the probe 101 includes first and second portions 600 and 601. The first portion 600 includes the transducer array 103, the drive system 104, the motor 115, the sensors 105, the controller 106, and a wireless interface 603. The second portion 601 includes the user interface 108 and a wireless interface 604. In this embodiment, the first and second portions 600 and 601 communicate with each other through the wireless interfaces 603 and 604.

In another embodiment, the controller 106 is located within a handle shield, which is formed as an external probe covering which acts also as a ground plane and heat distributor. In yet another embodiment, the controller 106 is incorporated within a handle in which in multiple components can be interchanged to provide a user or application specific probe. In still another embodiment, the controller 106 is part of independent circuitry which may be coupled to and employed with a plurality of different ultrasound probes, in conjunction with multiple different ultrasound imaging systems.

Figure 7:
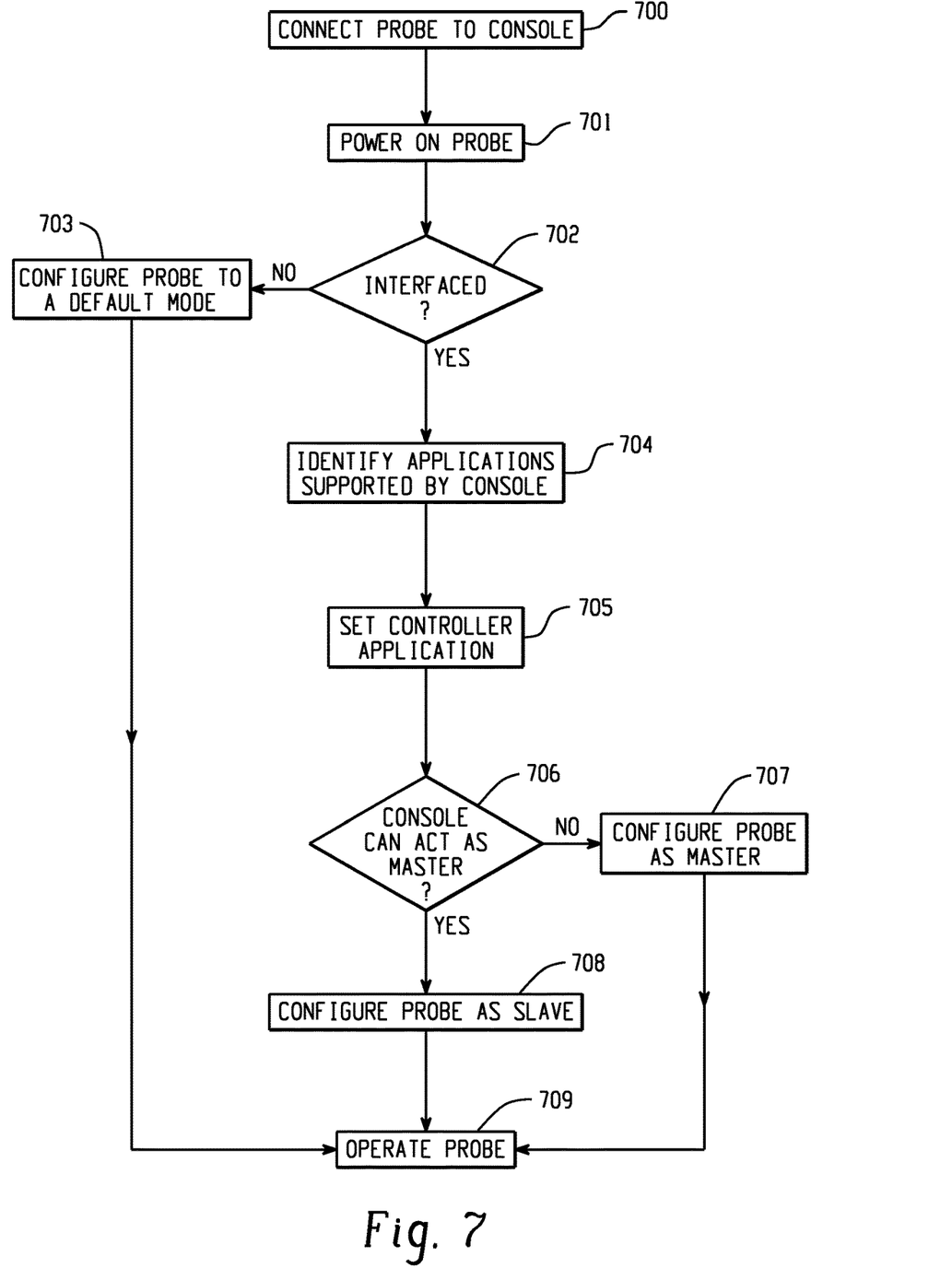
FIG. 7 illustrates one method for using an example probe and console of an imaging system.

FIG. 7 illustrates a method in connection with FIGS. 1-3 where the probe 101 is configured to communicate with the console 102 through a single interface.

At 700, the probe 101 is connected to the console 102.

At 701, the probe 101 is powered on. This can be achieved by activating a power switch or toggle of the user interface 108.

At 702, the probe 101 attempts communications with the console 102.

At 703, if the communication fails, the controller 106 places the probe 101 in a default mode, such as, the slave mode 302. In this mode, an application is selected and the probe 101 is controlled through the console 102.

At 704, if the communications is successful, the controller 106 identifies applications (two, three and/or four dimensions) supported by the console 102.

At 705, the controller 106 configures itself based on the identified supported applications. This includes allowing the probe 101 to be operated by the console 102 based on the applications supported by the console 102 and/or operated by the probe 101, including using applications that are not supported by the console 102.

At 706, the controller 106 determines whether the console 102 can act as a master device. At 707, if not, the probe 101 configures the probe 101 as a master device.

At 708, otherwise, the controller 106 configures the probe 101 as a slave device.

At 709, the probe 101 is employed based on user input to the probe 101, the console 102, and/or information sensed by the sensors 105.

Figure 8:
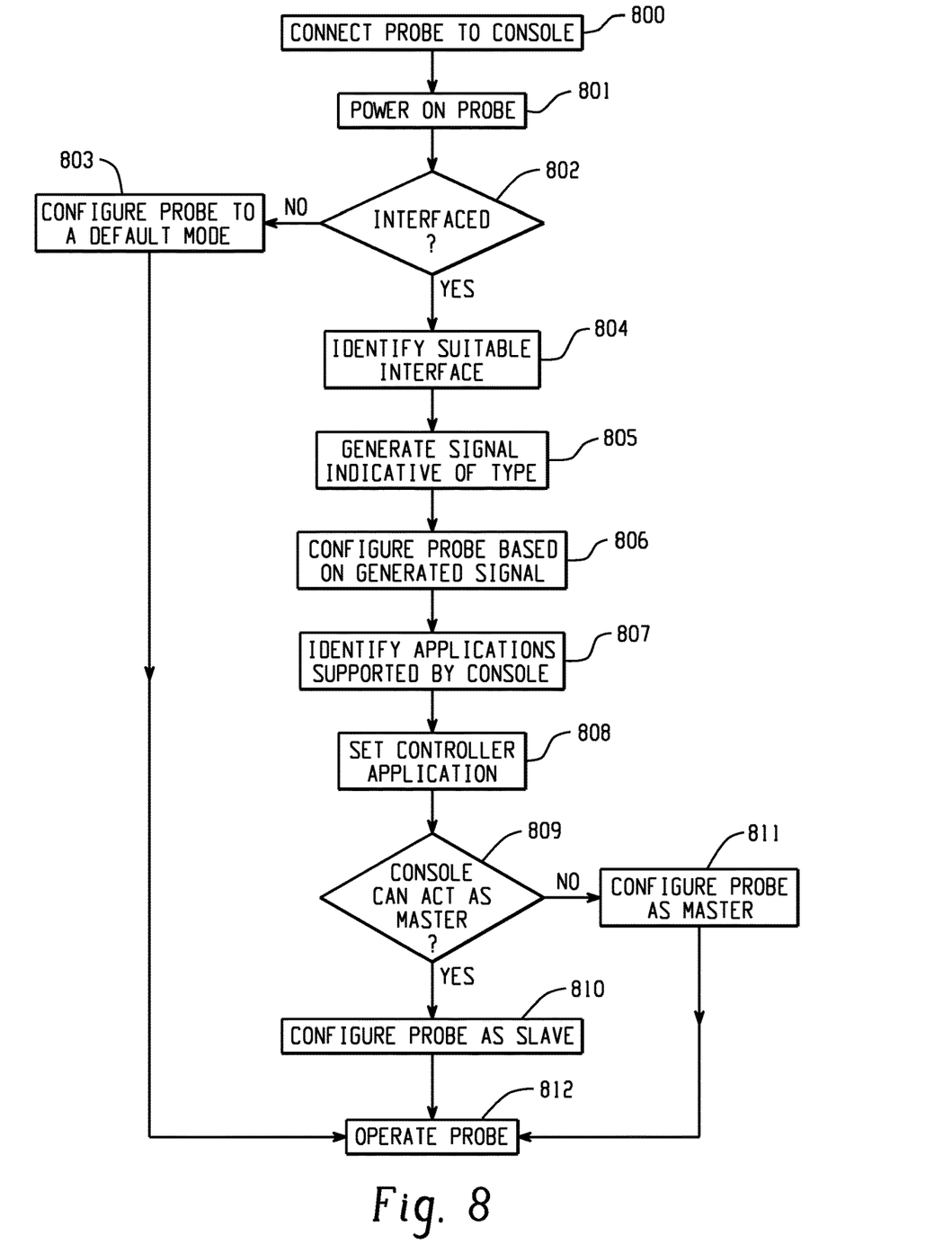
FIG. 8 illustrates a second method for using an example probe and console of an imaging system.

FIG. 8 illustrates a method in connection with FIGS. 1-3 where the probe 101 is configured to communicate with the console 102 through one or a plurality of different interfaces.

At 800, the probe 101 is connected to the console 102.

At 801, the probe 101 is powered on. This can be achieved by activating a power switch of the user interface 108.

At 802, the probe 101 attempts communications with the console 102.

At 803, if the communication fails, the controller 106 places the probe 101 in a default mode such as the master mode 301. In this mode, an application is selected and the probe 101 is controlled through the user interface 108.

At 804, if the communications is successful, the interface identifier 206 identifies the type of interface through which the probe 101 and console 102 are connected.

At 805, the interface identifier 206 generates a signal indicative of the identified type of interface.

At 806, the controller 106 configures the probe 101 to communicate based on the identified type of interface.

At 807, the controller 106 identifies applications (two, three and/or four dimensions) supported by the console 102.

At 808, the controller 106 configures itself based on the identified supported applications. This includes allowing the probe 101 to be operated by the console 102 based on the applications supported by the console 102 and/or operated by the probe 101, including using applications that are not supported by the console 102.

At 809, the controller 106 determines whether the console 102 can act as a master device. At 810, if so, the probe 101 configures the probe 101 as a slave device. Of course, the user can override this setting and/or the default settings may be that the probe 101 configures itself as the master device.

At 811, otherwise, the controller 106 configures the probe 101 as the master device.

At 812, the probe 101 is employed based on user input to the probe 101, the console 102, and/or information sensed by the sensors 105. Obtained data may be stored within a memory 109 of the probe 101 or transferred to the ultrasound console 102 or transmitted to other computing devices.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging probe, comprising:
  a movable transducer array with one or more transducer elements;
  a motor;
  an electromechanical drive configured to convert rotational motion of the motor into translational, rotational or wobbling movement of the transducer array to move, orient, or move and orient the movable transducer array with the motor for three- and four-dimensional ultrasound imaging applications;
  memory;
  a user interface;
  a communications interface, including two or more communication ports; and
  a controller configured to control the probe to acquire ultrasound data for the three- and four-dimensional ultrasound imaging applications, wherein the controller includes a microprocessor programmed to:
    transmit a communication through each of the two or more communication ports, wherein only one of the two or more communication ports is interfaced with an ultrasound console, wherein the ultrasound console is not part of the probe and does not include control circuitry configured to control the motor or the electromechanical drive for three- and four-dimensional applications;
    identify the only one of the two or more communication ports in response to the communication through the only one of the two or more communication ports being the only successful communication with the ultrasound console;
    communicate with the ultrasound console through the identified port to identify ultrasound imaging applications supported by the ultrasound console;

receive a signal from the user interface indicative of a user-selected ultrasound imaging application, wherein the user-selected application is selected from a group consisting of a three-dimensional ultrasound imaging application and a four-dimensional ultrasound imaging application;

generate a control signal to control the motor and the electromechanical drive for the selected ultrasound imaging application;

control the motor and the electromechanical drive with the control signal during execution of the selected ultrasound imaging application to move, orient, or move and orient the movable transducer array through the electromechanical drive during the three- or four-dimensional ultrasound imaging data acquisition; and store the acquired three- or four-dimensional ultrasound imaging data in the memory.

2. The probe of claim 1, wherein the microprocessor is further programmed to control the motor and the electromechanical drive during execution of an ultrasound imaging application supported by the ultrasound console.

3. The probe of claim 1, wherein the two or more communication ports are from a group consisting of an Inter-Integrated Circuit port, a Joint Action Test Group port, a Serial Peripheral Interface port, a Universal Serial Bus port, and a Radio Frequency Identification port.

4. The probe of claim 1, wherein the microprocessor is further programmed to control the motor based on an operation mode from a group consisting of a master mode and a slave mode.

5. The probe of claim 1, wherein the microprocessor is further programmed to control the motor based on an operation mode from a group consisting of a self-booting mode and a software loading mode.

6. The probe of claim 1, further comprising a temperature sensor that senses a temperature of a component of the probe.

7. The probe of claim 1, wherein the probe is a master device.

8. The probe of claim 1, wherein the probe is a slave device.

9. The probe of claim 2, further comprising:
a housing, wherein the electromechanical drive is housed in a portion of the housing that houses the motor.

10. The probe of claim 1, further comprising an optical and/or magnetic encoder that determines an orientation of the probe.

11. The probe of claim 1, further comprising a needle guide bracket mounted to the probe.

12. A method, comprising:
transmitting, via a communication interface of an ultrasound probe, a communications signal to a console via at least two different ports of the communication interface, wherein each of the at least two different ports is configured to support a different communication protocol;

identifying, via a configured microprocessor of a controller of the probe, a type of a port of at least two different ports through which the communication to the console was successful;

configuring, by the configured microprocessor of the probe, the controller to communicate with the console with a communication protocol for the type of the port and over the port;

configuring, via the configured microprocessor, the controller to operate via input to a user interface of the probe to perform a multi-dimensional ultrasound imaging applications, wherein the console does not support multi-dimensional ultrasound imaging applications;

receiving, via the configured microprocessor, a signal from the user interface indicative of a selection of a multi-dimensional ultrasound imaging application of the multi-dimensional ultrasound imaging applications;

acquiring, with a transducer array of the probe, multi-dimensional ultrasound imaging data based on the input; and storing, by the configured microprocessor, the acquired multi-dimensional ultrasound imaging data in a memory device of the probe.

13. The method of claim 12, wherein the multi-dimensional ultrasound imaging application is selected from a group consisting of a three-dimensional ultrasound imaging application and a four-dimensional ultrasound imaging application.

14. The method of claim 12, further comprising:
connecting the communication interface of the ultrasound probe to a communication interface of the console prior to transmitting the communications signal.

15. The method of claim 12, further comprising:
determining, via the configured microprocessor and through the port, ultrasound imaging applications supported by the console; and
configuring, via the configured microprocessor, the controller to operate via signals from the console to perform the ultrasound imaging applications supported by the console.

16. The method of claim 12, further comprising:
configuring, via the configured microprocessor, the controller to operate in a slave mode.

17. The method of claim 16, further comprising:
receiving, via the configured microprocessor, a change of mode signal; and
changing the mode from the slave mode to a master mode.

18. The method of claim 12, further comprising:
configuring, via the configured microprocessor, the controller to operate in a master mode.

19. The method of claim 18, further comprising:
receiving, via the configured microprocessor, a change of mode signal; and
changing the mode from the master mode to a slave mode.

20. A non-transitory computer readable storage medium encoded with computer executable instructions, which, when executed by a processor, cause the processor to:
transmit a communications signal to a console via at least two different ports of a communication interface, wherein each of the at least two different ports is configured to support a different communication protocol;

identify a type of a port of the at least two different ports through which the communication to the console was successful;

configure a controller to communicate with the console with a communication protocol for the type of the port and over the port;

configure, via input, the controller to operate a user interface of a probe to perform a multi-dimensional ultrasound imaging applications, wherein the console does not support multi-dimensional ultrasound imaging applications;

receive, via the user interface, a signal indicative of a selection of a multi-dimensional ultrasound imaging application of the multi-dimensional ultrasound imaging applications;

acquire multi-dimensional ultrasound imaging data based on the received signal; and store the acquired multi-dimensional ultrasound imaging data in a memory device of the probe.

\* \* \* \* \*